United States Patent
Cocconi et al.

(10) Patent No.: US 9,132,121 B2
(45) Date of Patent: Sep. 15, 2015

(54) DRY POWDER FORMULATION COMPRISING A PHOSPHODIESTERASE INHIBITOR

(75) Inventors: Daniela Cocconi, Parma (IT); Francesca Schiaretti, Parma (IT); Roberto Bilzi, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 13/195,885

(22) Filed: Aug. 2, 2011

(65) Prior Publication Data
US 2012/0031403 A1 Feb. 9, 2012

(30) Foreign Application Priority Data

Aug. 3, 2010 (EP) .................................. 10171748

(51) Int. Cl.
*A61M 16/00* (2006.01)
*A61K 31/44* (2006.01)
*A61K 9/00* (2006.01)
*A61K 9/14* (2006.01)

(52) U.S. Cl.
CPC .............. *A61K 31/44* (2013.01); *A61K 9/0075* (2013.01); *A61K 9/145* (2013.01)

(58) Field of Classification Search
CPC .................................................... A61K 9/0075
See application file for complete search history.

(56) References Cited

U.S. PATENT DOCUMENTS

2010/0129363 A1 * 5/2010 Zeldis et al. ............... 424/133.1

FOREIGN PATENT DOCUMENTS

| EP | 2 070 913 | 6/2009 | |
| EP | 2 216 327 | 8/2010 | |
| WO | WO 01/78693 | * 10/2001 | ............... A61K 9/72 |
| WO | WO 2005/115466 A1 | 12/2005 | |
| WO | 2006/131452 | 12/2006 | |
| WO | 2009/018909 | 2/2009 | |

OTHER PUBLICATIONS

European Search Report in Application No. 10171748.6, issued Jan. 14, 2011.
U.S. Appl. No. 13/488,818, filed Jun. 5, 2012, Armani, et al.
Office Action dated Dec. 1, 2014 issued in corresponding Colombian patent application No. 13019325.

* cited by examiner

*Primary Examiner* — Hasan Ahmed
(74) *Attorney, Agent, or Firm* — Oblon, McClelland, Maier & Neustadt, L.L.P.

(57) ABSTRACT

Pharmaceutical formulations in the form of inhalable dry powder comprising particles of a phosphodiesterase-4 inhibitor as active ingredient are useful for the prevention and/or treatment of respiratory diseases, such as asthma and COPD.

22 Claims, No Drawings

DRY POWDER FORMULATION COMPRISING A PHOSPHODIESTERASE INHIBITOR

CROSS REFERENCES TO RELATED APPLICATIONS

This application claims priority to European Patent Application No. 10171748.6, filed on Aug. 3, 2010, which is incorporated herein by reference in its entirety.

BACKGROUND OF THE INVENTION

1. Field of the Invention

The present invention relates to dry powder formulations suitable for the inhalatory administration by means of a dry powder inhaler. The present invention also relates to processes for the preparation of such a formulation, and to the use of such a formulation for the prevention and/or treatment of an inflammatory or obstructive airways disease such as asthma and COPD.

2. Discussion of the Background

Airway obstruction characterizes a number of severe respiratory diseases including asthma and chronic obstructive pulmonary disease (COPD). Events leading to airway obstruction include edema of airway walls, increased mucous production and inflammation.

Drugs for treating respiratory diseases such as asthma and COPD are currently administered through inhalation. One of the advantages of the inhalatory route over the systemic one is the possibility of delivering the drug directly at site of action, avoiding any systemic side-effects, thus providing a more rapid clinical response and a higher therapeutic ratio.

An important class of therapeutic agents which are under investigation in view of its anti-inflammatory effects for the treatment of inflammatory respiratory diseases is represented by the inhibitors of the phosphodiesterase enzymes (PDEs), in particular inhibitors of the phosphodiesterase type 4 (hereinafter referred to as PDE4).

Various compounds acting as PDE4 inhibitors have been disclosed. However, the usefulness of several PDE4 inhibitors of the first-generation such as rolipram and piclamilast has been limited because of their undesirable side effects such as nausea, gastric acid secretion and emesis due to their action on PDE4 in the central nervous system and due to the action on PDE4 in parietal cells in the gut.

The cause of said side effects has been widely investigated. It has been found that PDE4 exists in two distinct forms representing different conformations, that were designated as high affinity rolipram binding site or HPDE4, especially present in the central nervous system and in parietal cells, and low affinity rolipram binding site or LPDE4 (see Jacobitz, S et al., *Mol. Pharmacol.*, 1996, 50, 891-899, which is incorporated herein by reference in its entirety), which is found in the immune and inflammatory cells. While both forms appear to exhibit catalytic activity, they differ with respect to their sensitivity to inhibitors. In particular, compounds with higher affinity for LPDE4 appear less prone to induce side-effects such as nausea, emesis, and increased gastric secretion.

Thus, it would be advantageous to provide selective inhibitors of the LPDE4 form, therapeutically effective upon administration by inhalation.

Compounds with selective LPDE4 inhibition activity are disclosed in WO 2009/018909, which is incorporated herein by reference in its entirety. Additional PDE4 inhibitors having high potency are an object of the co-pending International Patent Application No. PCT/EP2010/000676 (which is incorporated herein by reference in its entirety), wherein it has been surprisingly found that the presence of sulphonamido substituents on the benzoate residue markedly improves the potency and that the (−) enantiomers are more potent than the corresponding (+) enantiomers and racemates. Moreover, it has been found that they could act in a synergistic way in combination with long-acting $\beta_2$-agonists.

Therefore these compounds may provide significant therapeutic benefit in the treatment of respiratory diseases such as asthma and COPD, when administered by inhalation.

Thus, there remains a need for formulations for delivering such compounds by inhalation.

SUMMARY OF THE INVENTION

Accordingly, it is one object of the present invention to provide novel formulations for delivering phosphodiesterase-4 inhibitor by inhalation.

It is another object of the present invention to provide novel processes for preparing such a formulation.

It is another object of the present invention to provide novel dry powder inhalers which contain such a formulation.

It is another object of the present invention to provided novel methods for the prevention and/or treatment of an inflammatory or obstructive airways disease such as asthma and COPD by administering such a formulation.

These and other objects, which will become apparent during the following detailed description, have been achieved by the inventors' discovery that pharmaceutical formulations in the form of an inhalable dry powder comprising micronized particles of a compound of general formula (I) as active ingredient, and particles of a physiologically acceptable pharmacologically-inert solid carrier may be administered by inhalation.

Thus, a first aspect of the present invention provides a pharmaceutical formulation in the form of inhalable dry powder comprising micronized particles of a compound of general formula (I), or a pharmaceutically acceptable salt thereof, as active ingredient, and particles of a physiologically acceptable pharmacologically-inert solid carrier.

According to another aspect, the present invention provides a dry powder inhaler comprising with the inhalable dry powder of the present invention.

A further aspect of the present invention provides inhalable dry powder of the present invention for use for the prevention and/or treatment of an inflammatory or obstructive airways disease such as asthma or chronic obstructive pulmonary disease (COPD).

A still further aspect of the present invention provides a method of preventing and/or treating an inflammatory or obstructive airways disease such as asthma or chronic obstructive pulmonary disease (COPD), which comprises administration by inhalation of a therapeutically effective amount of the inhalable dry powder of the present invention.

Finally the present invention also provides a package comprising an inhalable dry powder formulation of the present invention and a dry powder inhaler.

The inventors have discovered that phosphodiesterase-4 inhibitors may be administered to the respiratory tract by inhalation in the form of a dry powder by means of suitable inhalers known as dry powder inhalers (DPIs).

The aim of the present invention is to provide an inhalable dry powder composition that comprises a compound of general formula (I) acting as PDE4 inhibitor, as active ingredient.

Optimally such formulations shall exhibit good flowability, good uniformity of distribution of the active ingredient and adequate chemical and physical stability in the device before use. Such formulations shall also give rise to a good respirable fraction as well as deliver an accurate therapeutically active dose of the active ingredient.

DETAILED DESCRIPTION OF THE PREFERRED EMBODIMENTS

The terms "active drug," "active ingredient," "active," "active substance," "active compound," and "therapeutic agent" are used synonymously.

The term "substantially pure" means a compound having an optical purity higher than 90% based on the weight of said compound, advantageously higher than 95% w/w preferably higher than 97% w/w, more preferably higher than 97.5% w/w.

By "single therapeutically effective dose" it is meant the quantity of active ingredient administered at one time by inhalation upon actuation of the inhaler. Said dose may be delivered in one or more actuations, preferably one actuation (shot) of the inhaler. For "actuation" it is meant the release of active ingredient from the device by a single activation (e.g. mechanical or breath).

In general terms, the particle size of particles is quantified by measuring a characteristic equivalent sphere diameter, known as volume diameter, by laser diffraction. The particle size can also be quantified by measuring the mass diameter by means of suitable known instrument such as, for instance the sieve analyzer.

The volume diameter (VD) is related to the mass diameter (MD) by the density of the particles (assuming a size independent density for the particles).

In the present application, the particle size is expressed in terms of mass diameter (MD) and the particle size distribution is expressed in terms of: i) the mass median diameter (MMD) which corresponds to the diameter of 50 percent by weight or volume respectively, of the particles, and ii) the MD in micron of 10% and 90% of the particles, respectively.

The terms MMD and mean particle size are used synonymously.

The term "good flowability" refers to a formulation that is easy handled during the manufacturing process and is able to ensure an accurate and reproducible delivering of the therapeutically effective dose.

Flow characteristics can be evaluated by measuring the Can's index; a Can's index of less than 25 is usually taken to indicate good flow characteristics.

The expression "good homogeneity" refers to a formulation wherein, upon mixing, the content uniformity of the active ingredient, expressed as relative standard deviation (RSD), is less than 7.5%, preferably equal to or less than 5.0%.

The expression "chemically stable" refers to a formulation that meets the requirements of the ICH Guideline Q1A referring to "Stability Testing of new Active Substances (and Medicinal Products)," which is incorporated herein by reference inits entirety.

The expression "physically stable in the device before use" refers to a formulation wherein the active particles do not substantially segregate and/or detach from the surface of the carrier particles during fabrication of the dry powder and in the delivery device before use.

The tendency to segregate can be evaluated according to Staniforth et al., *J. Pharm. Pharmacol.*, 34,700-706, 1982, which is incorporated herein by reference in its entirety, and it is considered acceptable if the distribution of the active ingredient in the powder formulation after the test, expressed as relative standard deviation (RSD), does not change significantly with respect to that of the formulation before the test.

The expression "respirable fraction" refers to an index of the percentage of active particles which would reach the deep lungs in a patient.

The respirable fraction, also termed fine particle fraction, is evaluated using a suitable in vitro apparata such as Multistage Cascade Impactor or Multi Stage Liquid Impinger (MLSI) according to procedures reported in common Pharmacopeias. It is calculated by the ratio between the delivered dose and the fine particle mass (formerly fine particle dose).

The delivered dose is calculated from the cumulative deposition in the apparatus, while the fine particle mass is calculated from the deposition on Stages 3 (S3) to filter (AF) corresponding to particles ≤4.7 microns.

A respirable fraction higher than 30% is an index of good inhalatory performance.

The expression "accurate therapeutically active dose of the active ingredient" refers to a formulation wherein the variation between the mean delivered daily dose and the mean emitted dose is equal to or less than 15%, preferably less than 10%.

The compositions of the present invention are pharmaceutical formulations in the form of inhalable dry powder comprising micronized particles of a compound of general formula (I) as (−) enantiomer:

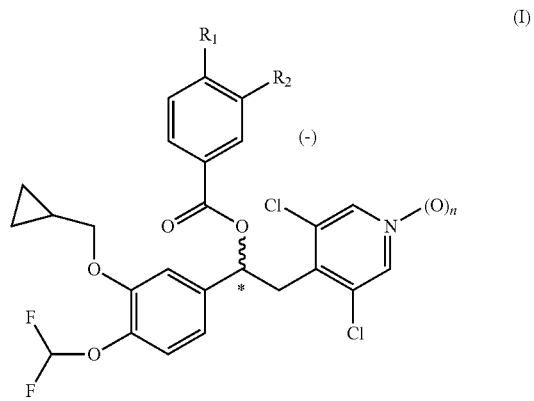

wherein:
n is 0 or 1;
$R_1$ and $R_2$ may be the same or different, and are selected from the group consisting of:
linear or branched ($C_1$-$C_6$)alkyl, optionally substituted by one or more halogen atoms;
—$OR_3$ wherein $R_3$ is a linear or branched ($C_1$-$C_6$)alkyl optionally substituted with one or more halogen atoms or $C_3$-$C_7$ cycloalkyl groups; and
—$HNSO_2R_4$ wherein $R_4$ is a linear or branched ($C_1$-$C_4$) alkyl optionally substituted with one or more halogen atoms, wherein at least one of $R_1$ and $R_2$ is —$HNSO_2R_4$; and
particles of a physiologically acceptable pharmacologically-inert solid carrier.

In the context of the present invention, the compounds of general formula (I) are used in the form of substantially pure (−)-enantiomer.

According to a preferred embodiment, the compound of general formula (I) is selected from the compounds C1, C2, C3, C4, C5 and C6 reported below.

| Compound | Chemical name |
|---|---|
| C1 | (−)-3-Cyclopropylmethoxy-4-methanesulfonylamino-benzoic acid 1-(3-cyclopropylmethoxy-4-difluoromethoxy-phenyl)-2-(3,5-dichloro-pyridin-4-yl)-ethyl ester |
| C2 | (−)-3-Cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester |
| C3 | (−)-4-Cyclopropylmethoxy-3-methanesulfonylamino-benzoic acid 1-(3-cyclopropylmethoxy-4-difluoromethoxy-phenyl)-2-(3,5-dichloro-1-oxy-pyridin-4-yl)-ethyl ester |
| C4 | (−)-3,4-Bis-methanesulfonylamino-benzoic acid 1-(3-cyclopropyl-methoxy-4-difluoromethoxy-phenyl)-2-(3,5-dichloro-1-oxy-pyridin-4-yl)-ethyl ester |
| C5 | (−)-3-Methanesulfonylamino-4-methyl-benzoic acid 1-(3-cyclopropyl-methoxy-4-difluoromethoxy-phenyl)-2-(3,5-dichloro-1-oxy-pyridin-4-yl)-ethyl ester |
| C6 | (−)-4-Methanesulfonylamino-3-methyl-benzoic acid 1-(3-cyclopropylmethoxy-4-difluoromethoxy-phenyl)-2-(3,5-dichloro-1-oxy-pyridin-4-yl)-ethyl ester |

In another embodiment, the preferred compound is C1. In another embodiment, the preferred compound is C2. In further preferred embodiments, the compound might be C3, C4, C5 or C6.

The compositions according to the present invention comprise the active ingredient in an amount such that, in case of administration by inhalation from inhalers, the therapeutically effective single dose (hereinafter the single dose) of a compound of general formula (I) is advantageously 10 μg to 2000 μg, more advantageously 20 μg to 1000 μg, preferably 50 μg to 800 μg, more preferably 80 to 700 μg and even more preferably 100 to 600 μg.

According to a preferred embodiment, the single dose may be 100 to 300 μg, while according to another preferred embodiment, the single dose may be 200 to 800 μg, more preferably 300 to 600 μg.

In other embodiments, the single dose may be 100 μg, 200 μg, 400 μg, or 600 μg

The single dose will depend on the kind and the severity of the disease and the conditions (weight, sex, age) of the patient and shall be administered one or more times a day, preferably once or twice a day.

The daily dose at which the pharmaceutical composition comprising a compound of general formula (I) shall be 100 μg to 1600 μg, preferably 200 μg to 800 μg and more preferably 200 μg to 600 μg.

In one embodiment, the daily dose may be reached by a single or double administration.

In another preferred embodiment, the daily dose may be reached by a single administration and delivered in one actuation of the inhaler.

In another preferred embodiment, the daily dose may be reached by a single administration and delivered in more actuations of the inhaler, preferably two.

In another preferred embodiment, the daily dose may be reached by a double administration and delivered in one actuation of the inhaler.

In another preferred embodiment, the daily dose may be reached by a double administration and delivered in more actuations of the inhaler, preferably two.

The particles of the compound of general formula (I) in the formulation according to the invention must be in a finely divided (micronized) form, i.e. their mass median diameter should generally be equal to or less than 10 microns, preferably less than 6 microns, more preferably 1 to 6 microns.

In certain embodiments of the invention, the particle size may fulfill the following requirements:
 i) no more than 10% of the particles have a mass diameter lower than 0.8 microns;
 ii) no more than 50% of particles have a mass diameter lower than 1.7 microns, preferably 1.8 to 2.5 microns; and
 iii) at least 90% of the particles have a mass diameter lower than 6 microns.

The active ingredient may be produced in the desired particle size using known methods, e.g. milling, direct precipitation, spray-drying, freeze-drying, or supercritical fluids.

The carrier particles may be made of any physiologically acceptable pharmacologically-inert material or combination of materials suitable for inhalatory use.

For example, the carrier particles may be composed of one or more materials selected from sugar alcohols; polyols, for example sorbitol, mannitol, and xylitol, and crystalline sugars, including monosaccharides and disaccharides; inorganic salts such as sodium chloride and calcium carbonate; organic salts such as sodium lactate; and other organic compounds such as urea, polysaccharides, for example starch and its derivatives; oligosaccharides, for example cyclodextrins and dextrins.

Advantageously the carrier particles are made of a crystalline sugar, for example, a monosaccharide such as glucose or arabinose, or a disaccharide such as maltose, saccharose, dextrose, or lactose.

Preferably, the carrier particles are made of lactose, more preferably of alpha-lactose monohydrate.

In one embodiment of the present invention, the powder formulation may be in form of agglomerated spheronized particles, also known as soft pellets, wherein the particles of a compound of general formula (I) and the particles of the carrier are both in a finely divided form, i.e. their mass median diameter is generally less than 10 microns, preferably from 1 to 6 microns.

Said formulations may be prepared according to known methods. Generally the process comprises the steps of:
 i) micronizing together the active ingredient and the carrier; and
 ii) subjecting the resulting co-micronized mixture to agglomeration and spheronization.

Alternatively, the process comprises the following steps:
 i) micronizing separately the active ingredient and the carrier;
 ii) mixing the micronized components; and
 iii) subjecting the resulting mixture to agglomeration and spheronization.

In another embodiment of the present invention, the formulation comprises coarse particles of a carrier together with the drug in the finely divided form, a type of formulation known in the art as an ordered mixture.

Advantageously, said carrier coarse particles have a mass diameter (MD) of at least 50 microns, more advantageously greater that 80 microns. Preferably, the MD is 90 microns to 500 microns. In certain embodiments of the invention, the MD may be 90 to 150 microns. In other embodiments, the MD may be 150 to 400 microns, with a MMD preferably greater than 175 microns, and more preferably the MD may be 210 to 355 microns.

The desired particle size may be obtained by sieving according to known methods.

When their MD is 150 to 400 microns, the carrier coarse particles have preferably a relatively highly fissured surface, that is, on which there are clefts and valleys and other recessed regions, referred to herein collectively as fissures. The "relatively highly fissured" coarse particles can be defined in terms of fissure index or rugosity coefficient as described in WO 01/78695 and WO 01/78693, which are both incorporated herein by reference in their entireties, and they can be characterized according to the description therein reported.

Said carrier coarse particles may also be characterized in terms of tapped density or total intrusion volume measured as reported in WO 01/78695, which is incorporated herein by reference in its entirety.

The tapped density of the carrier coarse particles is advantageously less than 0.8 g/cm$^3$, preferably 0.8 to 0.5 g/cm$^3$. The total intrusion volume is at least 0.8 cm$^3$ preferably at least 0.9 cm$^3$.

When the formulation of the present invention is in the form of the afore-mentioned ordered mixture, it may advantageously comprise an additive material capable of promoting the release of the active particles from the carrier particles on actuation of the inhaler device, and hence able of improving the respirable fraction. The additive material, which is preferably bound to the surface of the carrier coarse particles, is of a different material from the carrier particles.

Advantageously, the additive material is an amino acid, preferably selected from the group consisting of leucine, isoleucine, lysine, valine, methionine, and phenylalanine. The additive may be a salt of a derivative of an amino acid, for example aspartame or acesulfame K.

In one embodiment of the present invention, the additive particles consist substantially of leucine, advantageously L-leucine.

Alternatively, the additive material may include or consist of one or more water soluble surface active materials, for example lecithin, in particular soya lecithin.

In a particular embodiment of the present invention, the additive material may include or consist of one or more lubricants selected from the group consisting of stearic acid and salts thereof such as magnesium stearate, sodium lauryl sulphate, sodium stearyl fumarate, stearyl alcohol, and sucrose monopalmitate.

Other possible additive materials include talc, titanium dioxide, aluminium dioxide, and silicon dioxide.

Advantageously, the additive particles have a starting mean particle size of less than 35 microns. Preferably they have a mean particle size of not more than 15 microns, more preferably of not more than 10 microns.

The optimum amount of additive material shall depend on the chemical composition and other properties of the additive material.

In general, the amount of additive shall be not more than 10% by weight, based on the total weight of the formulation.

However, it is thought that for most additives the amount of additive material should be not more than 5% by weight, preferably not more than 2% by weight, or even not more than 1% by weight, or not more than 0.5% by weight, based on the total weight of the formulation. In general, the amount of additive material is at least 0.01% by weight based on the total weight of the formulation.

In one of the preferred embodiments of the present invention, the additive material is magnesium stearate.

The amount of magnesium stearate is generally 0.01 to 2% by weight, preferably 0.02 to 1% by weight, more preferably 0.1% to 0.5% by weight, based on the total weight of the formulation.

In some embodiments, magnesium stearate may coat the surface of the carrier particles in such a way as that the extent of the molecular surface coating is at least of 5%, preferably more than 10%, more preferably more than 15%, even more preferably equal to or more than and 25%.

The extent of molecular surface coating, which indicates the percentage of the total surface of the carrier particles coated by magnesium stearate, may be determined by water contact angle measurement as reported in WO 00/53157 or in the co-pending European Patent Application No. EP 10158951.3, both of which are incorporated herein by reference in their entireties.

For very high extents of surface coating, i.e. higher than 60%, the coating may be achieved using the process described in the co-pending European Patent Application No. EP 10158951.3, cited above.

The extent to which the magnesium stearate coats the surface of the lactose particles may also be determined by scanning electron microscopy (SEM), a versatile analytical technique well known in the art. Such microscopy may be equipped with an EDX analyzer (an Electron Dispersive X-ray analyzer), that can produce an image selective to certain types of atoms, for example magnesium atoms. In this manner it is possible to obtain a clear data set on the distribution of magnesium stearate on the surface of carrier particles. SEM may alternatively be combined with IR or Raman spectroscopy for determining the extent of coating, according to known procedures.

Another analytical technique that can advantageously be used is X-ray photoelectron spectroscopy (XPS), by which it has been possible to calculate both the extent of coating and the depth of the magnesium sterate film around the lactose particles. XPS measurements may be taken with commercially available instruments such as Axis-Ultra instrument from Kratos Analytical (Manchester UK), typically using monochromated A1 Kα radiation according to known procedures.

The formulations of the present invention in the form of an ordered mixture may also comprise fine particles of a physiologically acceptable pharmacologically-inert material with a mass median diameter (MMD) equal to or less than 15 microns, preferably equal to or less than 10 microns, even more preferably equal to or less than 6 microns.

The percentage of fine particles of physiologically acceptable pharmacologically-inert material is advantageously 0.1 to 40% by weight of the total amount of the formulation.

Preferably, the coarse particles and the fine particles are constituted of the same physiologically acceptable pharmacologically-inert material.

In a preferred embodiment of the present invention, in particular when the single dose of the active ingredient is equal to or less than 300 μg, preferably equal to or less than 200 μg, the formulation is in form of hard-pellets according to the teaching of WO 01/78693, which is incorporated herein by reference in its entirety.

Said formulation comprises:

i) particles of a compound of general formula (I) in a micronized form;

ii) a fraction of microparticles constituted of a mixture composed of particles of physiologically acceptable pharmacologically-inert material and particles of an additive material, said microparticles having a MMD equal to or less than 10 microns, preferably equal to or less than 6 microns; and iii) a fraction of particles of a physiologically acceptable pharmacologically-inert material having a highly fissured surface and a mass diameter (MD) of 150 microns to 400 microns, preferably 212 to 355 microns.

Advantageously the fraction of microparticles is composed of 90 to 99.5% by weight of the physiologically acceptable pharmacologically-inert material and 0.5 to 10% by weight of the additive material, and the ratio between the fraction of microparticles and the fraction of coarse particles is 1:99 to 40:60% by weight, preferably 5:95 to 30:70% by weight, even more preferably 10:90 to 20:80% by weight.

Preferably the physiologically acceptable inert material is α-lactose monohydrate, and the additive material is magnesium stearate.

In a more preferred embodiment, the fraction of microparticles is composed of 98 to 99% by weight of α-lactose monohydrate and 1 to 2% by weight of magnesium stearate, and the ratio between the fraction of microparticles and the fraction of coarse particles made of α-lactose monohydrate is 10:90% by weight, respectively.

The amount of magnesium stearate in the final formulation is advantageously 0.01 to 1.0% by weight, preferably 0.05 to 0.5% by weight, more preferably 0.1 to 0.4% by weight, based on the total weight of the formulation.

The formulation in form of an ordered mixture according to the invention may be prepared according to known methods. Said methods comprise the step of mixing together the carrier coarse particles, the optional fine carrier particles and the additive particles, and finally adding the finely divided pharmaceutically active compound to the resulting mixture.

The particularly preferred formulation according to the invention may be prepared according to the methods reported in WO 01/78693, which is incorporated herein by reference in its entirety. Among the methods therein described, the formulation is preferably prepared according to a process which comprises the following steps:

a) preparing microparticles constituted of a mixture composed of particles made of physiologically acceptable pharmacologically-inert material and particles of the additive, the inert material and the additive being first-mixed together and then co-micronized;

b) mixing the microparticles of step a) with coarse particles of a physiologically acceptable pharmacologically-inert material such that microparticles adhere to the surface of the coarse particles;

c) adding by mixing the active particles in the micronized form to the particles of step b).

The co-micronization step may be carried out by known methods, e.g. as reported in WO 02/00197, which is incorporated herein by reference in its entirety.

Advantageously, said step is carrier out by milling, more preferably by using a jet mill according to the conditions reported in WO 01/78693, which is incorporated herein by reference in its entirety.

In a particular embodiment, the microparticles of step a) obtained by co-micronization may be subjected to a conditioning step according to conditions disclosed in the co-pending European Patent Application No. EP 10160565.7, which is incorporated herein by reference in its entirety.

Advantageously during the step a) the additive may be embedded in the formed microparticles, or alternatively, in the case of a lubricant such as magnesium stearate, the additive may coat the surface of the carrier particles in such a way that the extent of molecular surface coating is at least of 5%, preferably more than 10%, more preferably more than 15%, even more preferably more than and 35%.

The extent of molecular surface coating indicates the percentage of the total surface of the carrier particles coated by magnesium stearate.

The presence of the additive material embedded in the microparticles may be detected according to known methods, for instance, by electron scanning microscope coupled to microcalorimetry.

Alternatively, as reported above, the extent of molecular surface coating may be determined by water contact angle measurement as reported in WO 00/53157, which is incorporated herein by reference in its entirety, or by other known tools.

The formulations of the present invention may further comprise other therapeutic agents useful for the prevention and/or treatment of a respiratory disease, e.g. beta$_2$-agonists such as salbutamol, salmeterol, and vilanterol; corticosteroids such as fluticasone propionate or furoate, flunisolide, mometasone furoate, rofleponide and ciclesonide; anticholinergic or antimuscarinic agents such as ipratropium bromide, oxytropium bromide, tiotropium bromide, oxybutynin, and combinations thereof.

The dry powder formulation herein described may be used in all customary dry powder inhalers such as unit dose or multidose inhalers.

For example, the formulation of the invention may be filled in hard gelatine capsules, in turn loaded in a unit dose inhaler such as the Aerolizer™. Alternatively, the formulation as a powder may be filled in a multidose inhaler comprising a powder reservoir such as that described in WO 2004/012801, which is incorporated herein by reference in its entirety.

Administration of the formulations of the invention may be indicated for the prevention and/or the treatment of mild, moderate or severe acute or chronic symptoms or for prophylactic treatment of an inflammatory or obstructive airways disease such as asthma and chronic obstructive pulmonary disease (COPD).

Other respiratory disorders characterized by obstruction of the peripheral airways as a result of inflammation and presence of mucus such as chronic obstructive bronchiolitis and chronic bronchitis may also benefit from the formulation of the invention.

Other features of the invention will become apparent in the course of the following descriptions of exemplary embodiments which are given for illustration of the invention and are not intended to be limiting thereof.

EXAMPLES

Example 1

Inhalable Dry Powder Formulation Comprising Compound C2 (Formulation 1)

A powder formulation according to the invention has the composition reported in Table 1.

TABLE 1

| | Amounts | | |
|---|---|---|---|
| | Per shot of the inhaler | | Single dose |
| Components | mg | % | μg |
| Compound C2 | 0.2 | 1.0 | 200 |
| Alpha-lactose monohydrate 212-355 μm | 17.82 | 89.1 | |
| Co-micronised particles | 1.98 | 9.9 | |
| Total weight | 20 | | |

A 1 kg batch size of the dry powder formulation was prepared as described as follows. Crystalline (−)-3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester (compound C2) was micronized by methods known in the art, to prepare the active substance in the form of particles having a typical particle size suitable for inhalation. Particles of α-lactose monohydrate having a mean particle size of less than 250 microns, and magnesium stearate particles having a mean particle size of less than 35 microns in a ratio 98:2 percent by weight were co-micronized by milling in a jet mill operating under nitrogen to obtain the fraction of co-micronized particles indicated as co-micronised particles. The co-micronized particles were mixed with fissured coarse particles of α-lactose monohydrate having a mass diameter of 212 to 355 microns, and obtained by sieving, in the ratio 90:10 percent by weight. The mixing was carried out in a Turbula mixer for 4 hours.

To a part of the obtained mixture, the micronized compound C2 was added, and the resulting mixture was sieved through 250 μm mesh. The remaining part of the above mixture was added and mixed in a Turbula mixer for 90 minutes at 32 r.p.m to give the final formulation. The final formulation was filled in hard gelatin capsules and loaded in the Aerolizer™ inhaler.

The aerosol performances were evaluated using a Multi Stage Liquid Impinger (MSLI) according to the procedure described in European Pharmacopoeia $2^{nd}$ edition, 1995, part V. 5.9.1, pages 15-17, which is incorporated herein by reference in its entirety. The results in terms of delivered dose (DD), fine particle mass (FPM), fine particle fraction (FPF), and mass median aerodynamic diameter (MMAD) are reported in Table 2.

TABLE 2

| DD (μg) | FPM (μg) | FPF (%) | MMAD (μm) |
|---|---|---|---|
| 148.5 | 105.7 | 71.1 | 1.5 |

It can be appreciated that the formulation comprising C2 as active ingredient is capable of giving rise to an excellent fine respirable (FPF).

In a similar manner, formulations comprising compounds C1, C3, C4, C5 or C6 are prepared.

Example 2

Inhalable Dry Powder Formulation Comprising Compound C2 (Formulation 2)

A powder formulation with a similar composition of that of Example 1 was prepared but having the unitary composition, i.e. the composition per shot of the inhaler, reported in Table 3.

TABLE 3

| | Amounts | | |
|---|---|---|---|
| | Per shot of the inhaler | | Single dose |
| Components | mg | % | μg |
| Compound C2 | 0.1 | 1.0 | 100 |
| Alpha-lactose monohydrate 212-355 μm | 8.91 | 89.1 | |
| Co-micronised particles | 0.99 | 9.9 | |
| Total weight | 10 | | |

The formulation was filled in the multidose dry powder inhaler described in WO 2004/012801, which is incorporated herein by reference in its entirety. The aerosol performances were determined as reported in Example 1. The results are reported in Table 4.

TABLE 4

| DD (μg) | FPM (μg) | FPF (%) | MMAD (μm) |
|---|---|---|---|
| 96.9 | 65.1 | 67.2 | 1.2 |

Also, in this case the FPF turned out to be excellent, indicating that said kind of formulation is capable of providing good aerosol performances whatever inhaler is used.

Example 3

Inhalable Dry Powder Formulations Comprising Compound C2 (Formulations 3, 4, 5 and 6)

Powder formulations with a similar composition of that of Example 1 or Example 2 were prepared using different strengths and percentages of co-micronized particles. The compositions are reported in Table 5. The final formulations are filled in hard gelatin capsules and loaded in the Aerolizer™ inhaler. Similarly, powder formulations with the same relative percentage composition but for a unit dose of 10 mg are prepared and filled in the multidose dry powder inhaler described in WO 2004/012801, which is incorporated herein by reference in its entirety.

TABLE 5

| | Strength | | | |
|---|---|---|---|---|
| | 20 μg/20 mg | 20 μg/20 mg | 200 μg/ 20 mg | 400 μg/ 20 mg |
| α-lactose monohydrate 212-355 μm (mg) | 17.982 | 18.981 | 18.81 | 17.64 |
| α-lactose monohydrate 212-355 μm (%) | 89.9 | 94.9 | 94.0 | 88.0 |
| Co-micronized particles (mg) | 1.998 | 0.999 | 0.99 | 1.96 |
| Co-micronized particles (%) | 10 | 5 | 5 | 10 |
| Compound C2 (mg) | 0.020 | 0.020 | 0.200 | 0.400 |
| Compound C2 (%) | 0.1 | 0.1 | 1.0 | 2.0 |
| Total | 20 mg | 20 mg | 20 mg | 20 mg |

In a similar manner, formulations comprising compounds C1, C3, C4, C5 or C6 are prepared.

Example 4

Inhalable Dry Powder Formulations Comprising Compound C2 (Formulations 7 and 8)

Further powder formulations according to the invention are prepared with the compositions reported in Tables 6 and 7.

TABLE 6

| | Amounts | | |
|---|---|---|---|
| | Per shot of the inhaler | | Single dose |
| Components | mg | % | μg |
| Compound C2 | 0.100 | 1.0 | 100 |
| Alpha-lactose monohydrate 90-150 μm | 9.875 | 98.75 | |
| Magnesium stearate | 0.025 | 0.25 | |
| Total weight | 10 | | |

TABLE 7

| Components | Amounts | | Single dose |
|---|---|---|---|
| | Per shot of the inhaler | | |
| | mg | % | μg |
| Compound 1 | 0.200 | 2.0 | 200 |
| Alpha-lactose monohydrate 90-150 μm | 9.79 | 97.90 | |
| magnesium stearate | 0.01 | 0.10 | |
| Total weight | 10 | | |

In a similar manner, formulations comprising compounds C1, C3, C4, C5 or C6 are prepared.

Example 5

Assessment of the Anti-Inflammatory Activity of Compound C2

The potency of one of the preferred compounds of the present invention was evaluated in vivo in an acute model of lung inflammation following a method described in *Eur. J. Pharmacol.*, 2002 Feb. 22; 437(3): 187-94 (which is incorporated herein by reference in its entirety), with minor modifications. Briefly, male Brown-Norway rats (150-200 g) were sensitized by intraperitoneal injection of a suspension containing ovalbumin (OVA, 1 mg/rat) and $Al(OH)_3$ (100 mg/rat) in 1 mL of saline for 3 consecutive days. Two-three weeks later, the airway inflammation was induced by inhaled antigen (OVA, 1% in saline). Vehicle-control treated animals were exposed to an aerosol of saline. Aerosol challenge with OVA resulted in a statistically significant increase in neutrophil, eosinophil, and lymphocyte concentrations in bronchoalveolar lavage fluid (BALF), all hallmarks of acute ongoing pulmonary inflammation. For the detection of inhibitory potency, micronized compound C2 was blended with lactose at different concentrations and administered by the intratracheal route as single dose 2 hours before antigen aerosol.

A dose-response curve of the inhibitory effect of the test compound on OVA-induced eosinophilia in BALF was performed and the ED50 dose of compound C2 was taken as a measure of potency in this bioassay. The ED50 dose value for the compound C2 was 0.028 μmol/kg (0.016 to 0.051) of body weight, that should correspond to a human dose of 100 to 600 μg daily.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An inhalable dry powder formulation, comprising:
   (a) micronized particles of the (−) enantiomer of active ingredient 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester; and
   (b) particles of a carrier comprising a mixture of coarse particles comprised of alpha-lactose monohydrate having a mass diameter of 150 to 400 microns, finely divided particles comprised of alpha-lactose monohydrate having a mass median diameter (MMD) equal to or less than 10 microns, and magnesium stearate,
   wherein said active ingredient 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester is present in an amount such that administration by inhalation from an inhaler affords a single therapeutically effective dose of 600 μg to 2000 μg, and
   wherein said coarse particles of alpha-lactose monohydrate have a fissure index of at least 1.25.

2. The inhalable powder according to claim 1, which comprises magnesium stearate in an amount of 0.01 to 2% by weight, based on the total weight of said formulation.

3. The inhalable powder according to claim 1, which comprises magnesium stearate in an amount of 0.02 to 1% by weight, based on the total weight of said formulation.

4. A dry powder inhaler, comprising an inhalable dry powder formulation according to claim 1.

5. A package, comprising an inhalable dry powder formulation according to claim 1 and a dry powder inhaler.

6. A method for the treatment of a respiratory disease, comprising administering an effective amount of a formulation according to claim 1 to a subject in need thereof.

7. The method according to claim 6, wherein said respiratory disease is asthma or chronic obstructive pulmonary disease.

8. The method according to claim 6, wherein said at least one compound of general formula (I) is administered in a single dose of 600 μg to 2000 μg.

9. The method according to claim 6, wherein said at least one compound of formula (I) is administered in a single dose of 600 μg to 1000 μg.

10. The method according to claim 6, wherein said at least one compound of formula (I) is administered in a single dose of 600 μpg to 800 μg.

11. The method according to claim 6, wherein said at least one compound of formula (I) is administered in a single dose of 600 μg.

12. The inhalable powder according to claim 1, which comprises said 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester having an optical purity higher than 90% based on the weight of said 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester.

13. The inhalable powder according to claim 1, which comprises said 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester having an optical purity higher than 95% based on the weight of said 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester.

14. The inhalable powder according to claim 1, which comprises said 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester having an optical purity higher than 97% based on the weight of said 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester.

15. The inhalable powder according to claim 1, which comprises said 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester having an optical purity higher than 97.5% based on the weight of said 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester.

16. The inhalable powder according to claim 1, wherein said active ingredient 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester is present in an amount such that administration by inhalation from an inhaler affords a single therapeutically effective dose of 600 μg to 1000 μg.

17. The inhalable powder according to claim 1, wherein said active ingredient 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester is present in an amount such that administration by inhalation from an inhaler affords a single therapeutically effective dose of 600 μs to 800 μg.

18. The inhalable powder according to claim 1, wherein said active ingredient 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester is present in an amount such that administration by inhalation from an inhaler affords a single therapeutically effective dose of 600 μg.

19. The inhalable powder according to claim 1, wherein said coarse carrier particles have a mass diameter of 212 to 355 microns.

20. A dry powder unit dose inhaler, comprising an inhalable dry powder formulation according to claim 1.

21. A dry powder multidose inhaler, comprising an inhalable dry powder formulation according to claim 1.

22. The inhalable powder according to claim 1, which comprises said 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester having an optical purity higher than 90% based on the weight of said 3-cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester, and wherein said coarse carrier particles have a mass diameter of 212 to 355 microns.

* * * * *